(12) United States Patent
Faurissoux et al.

(10) Patent No.: US 11,441,995 B2
(45) Date of Patent: Sep. 13, 2022

(54) METHOD FOR DETERMINING A REPRESENTATIVE PARAMETER OF A POROUS SAMPLE AND RELATED ASSEMBLY

(71) Applicant: TOTAL SA, Courbevoie (FR)

(72) Inventors: Pierre Faurissoux, Pau (FR); Benjamin Nicot, Pau (FR); Ghislain Pujol, Pau (FR); Alison Colombian, Pau (FR)

(73) Assignee: TOTAL SA, Courbevoie (FR)

( * ) Notice: Subject to any disclaimer, the term of this patent is extended or adjusted under 35 U.S.C. 154(b) by 301 days.

(21) Appl. No.: 16/605,258

(22) PCT Filed: Apr. 21, 2017

(86) PCT No.: PCT/IB2017/000607
§ 371 (c)(1),
(2) Date: Oct. 15, 2019

(87) PCT Pub. No.: WO2018/193282
PCT Pub. Date: Oct. 25, 2018

(65) Prior Publication Data
US 2021/0148804 A1 May 20, 2021

(51) Int. Cl.
*G01N 15/00* (2006.01)
*G01N 15/08* (2006.01)
*G01N 33/24* (2006.01)

(52) U.S. Cl.
CPC ....... *G01N 15/0893* (2013.01); *G01N 33/241* (2013.01); *G01N 2015/0015* (2013.01); *G01N 2015/0034* (2013.01)

(58) Field of Classification Search
CPC ............. G01N 15/0893; G01N 33/241; G01N 2015/0015; G01N 15/0034; G01N 15/088;
(Continued)

(56) References Cited

U.S. PATENT DOCUMENTS 4,671,102 A * 6/1987 Vinegar ............... G01N 15/042
73/61.48
4,924,187 A 5/1990 Sprunt et al.
4,924,196 A 5/1990 Uyeda
(Continued)

OTHER PUBLICATIONS

Ramakrishnan, T.S. et al., "A new technique to measure static and dynamic properties of a partially saturated porous medium" Chemical Engineering Science, 46(4):1157-1163 (Jan. 1, 1991) cited in ISR & Written Opinion issued in Appln No. PCT/IB2017/000607 dated Jan. 2, 2018.
(Continued)

*Primary Examiner* — Patrick Assouad
*Assistant Examiner* — Sangkyung Lee
(74) *Attorney, Agent, or Firm* — Troutman Pepper Hamilton Sanders LLP

(57) ABSTRACT

The method comprises the following steps providing a porous sample containing a first fluid; establishing a steady state profile of a second fluid content in the porous sample by applying a first mechanical load, to create a plurality of regions having different second fluid contents in the porous sample; measuring, in each of the plurality of regions, a local saturation in the first fluid or/and in the second fluid; measuring, in each of the plurality of regions, a corresponding local electrical resistivity and/or conductivity; and determining a value of the representative parameter based on the corresponding values of local saturation and of local electrical conductivity and/or resistivity in each of the plurality of regions.

19 Claims, 6 Drawing Sheets

(58) Field of Classification Search
CPC ............... G01N 27/043; G01N 15/082; G01N 15/0806; G01V 3/02; C04B 38/005; B01D 63/061; B01D 63/063; B01D 63/066; B01D 67/0088
See application file for complete search history.

(56) References Cited

U.S. PATENT DOCUMENTS

| | | | |
|---|---|---|---|
| 5,253,529 A | 10/1993 | Lenormand et al. | |
| 7,642,774 B2 * | 1/2010 | Fleury | G01N 33/241 324/303 |
| 2006/0016828 A1 | 6/2006 | Chen et al. | |
| 2008/0203011 A1 * | 8/2008 | Lescoche | B01D 63/061 210/500.21 |

OTHER PUBLICATIONS

Wildenschild D. et al., "X-ray imaging and analysis techniques for quantifying pore-scale structure and processes in subsurface porous medium systems" Advances in Water Resources, 51:217-246 (Jul. 1, 2012) cited in ISR & Written Opinion issued in Appln No. PCT/IB2017/000607 dated Jan. 2, 2018.

International Search Report and Written Opinion issued in corresponding International Patent Application No. PCT/IB2017/000607 dated Jan. 2, 2018.

* cited by examiner

METHOD FOR DETERMINING A REPRESENTATIVE PARAMETER OF A POROUS SAMPLE AND RELATED ASSEMBLY

CROSS REFERENCE TO RELATED APPLICATION

This is a U.S. National Phase Application under 35 U.S.C. § 371 of International Patent Application No. PCT/IB2017/000607, filed Apr. 21, 2017. The entire contents of which are hereby incorporated by reference.

FIELD OF THE INVENTION

The present invention concerns a method for determining a representative parameter of a porous sample.

BACKGROUND

Such a method is used for example to determine the exponent coefficient n of the brine saturation $S_w$ in Archie's law. The method can also be used to additionally determine the capillary pressure Pc as a function of the brine saturation $S_w$ in a sample of formation extracted from a sub-soil.

The porous sample is for example a rock sample recovered from a sub-soil formation.

When drilling a well, it is known to recover solid samples from the formations through which the well is drilled, in particular rock samples.

These rock samples are used for obtaining a log of the successive geologic formations penetrated by the well.

The log is generally obtained by visual inspections of the samples recovered at the surface, and/or by physical measurements carried out along the well.

SUMMARY

In a logging operation, electrical conductivity is often measured. Electrical conductivity can be related to significant parameters of the formations, including in particular porosity and saturation.

For example, an empirical law such as Archie's law relates the electrical conductivity of a porous sample of formation to its porosity and to its brine saturation. In a fluid saturated rock, the brine saturation is then related to hydrocarbon saturation, providing extremely relevant information about the location and potential of hydrocarbon reservoirs after the well is drilled.

Archie's law, reformulated for electrical resistivity reads as follows:

$$R_t = a \times \Phi^{-m} \times S_w^{-n} \times R_w$$

in which $R_t$ is the sample resistivity, $R_w$ is the sample resistivity when saturated with brine, $\Phi$ is the sample porosity, and a is a constant.

The formation factor $R_0 = a \times \Phi^{-m} \times R_w$ is determined by measuring the resistivity of the porous sample saturated only with brine. As a consequence, a resistivity index RI can be determined following the following equation:

$$\log RI = \log\left(\frac{R_t}{R_0}\right) = -n \times \log S_w$$

In order to use Archie's law, the exponent coefficient n associated with the brine saturation $S_w$ has to be experimentally determined for a particular porous sample.

Experimental determination of Archie's law exponent coefficient n is generally a long and tedious process.

A porous sample containing water is inserted in a cell. Oil under pressure is injected in the porous sample, at one end of the porous sample, and another end of the porous sample is equipped with a porous plate from which only water is able to be extracted.

After a long time, generally in the order of a month, a steady state is reached in the porous sample. An average saturation $S_w$ in water of the porous sample is measured.

In parallel, the resistivity $R_t$ of the porous sample is measured by placing electrodes at the ends of the porous sample when the steady state is reached.

A first point of the curve connecting the logarithm of the saturation with the resistive index is thus obtained. The capillary pressure is here equal to the pressure at which the oil is injected and a first point of the curve of the capillary pressure versus saturation is obtained.

Then, the oil pressure is increased at the porous sample inlet. The experiment is stayed until a steady state is reached. When the steady state is reached, a second measurement of the resistivity and of the capillary pressure is carried out to obtain a second point of the above mentioned curve.

The previously described operations must then be repeated several times until an adequate number of points is determined.

As a consequence, the measurement of the determination of the exponent coefficient n of Archie's law and of the pressure of the capillary pressure Pc versus saturation takes several months. This significantly delays the log interpretation and the resultant business decisions for the operations.

One aim of the invention is to obtain a robust method for determining representative parameters of a formation sample, such as the saturation exponent n in Archie's law or/and the capillary pressure as a function of saturation, which is fast to operate.

To this aim, the subject-matter of the invention is a method of the afore-mentioned type, comprising the following steps:

- providing a porous sample containing a first fluid;
- establishing a steady state profile of a second fluid content in the porous sample by applying a first mechanical load, to create a plurality of regions having different second fluid contents in the porous sample;
- measuring, in each of the plurality of regions, a local saturation in the first fluid or/and in the second fluid;
- measuring, in each of the plurality of regions, a corresponding local electrical resistivity and/or conductivity;
- determining a value of the representative parameter based on the corresponding values of local saturation and of local electrical conductivity and/or resistivity in each of the plurality of regions.

The method according to the invention may comprise one or more of the following feature(s), taken solely or according to any technically feasible combination:

- the representative parameter is an exponent coefficient of the saturation in Archie's law;
- the determining of the representative parameter comprises calculating a slope of a curve of a logarithm resistive index calculated from the local resistivity measured in a plurality of regions, as a function of a logarithm of the local saturation in the first fluid or/and in the second fluid in each of the plurality of regions;

the mechanical load is applied by centrifugation of the porous sample;

the measuring, in each of the plurality of regions, of a local saturation in the first fluid or/and in the second fluid is carried out by nuclear magnetic resonance or/and by X-ray diffraction;

the measuring, in each of the plurality of regions, a corresponding local electrical resistivity and/or conductivity comprises placing electrodes locally at the boundaries of the region;

establishing the steady state profile in the porous sample comprises saturating the porous sample with the first fluid, and progressively introducing the second fluid into the porous sample while applying the mechanical load;

establishing the steady state profile comprises measuring the rate of second fluid and/or first fluid extracted from the porous sample;

it comprises, after measuring a plurality of local saturations in the first fluid or/and in the second fluid and after measuring a plurality of electronical conductivities and/or resistivities, applying an additional mechanical load to the porous sample to obtain a modified steady state profile of content in second fluid, the additional mechanical load having an intensity different from the first mechanical load, and measuring, in each of the plurality of regions, a local saturation in the first fluid or/and in the second fluid and a corresponding local electrical resistivity and/or conductivity after applying the additional mechanical load;

it comprises, after measuring a plurality of local saturations in the first fluid or/and in the second fluid and after measuring a plurality of electronical conductivities and/or resistivities, establishing a fluid content steady state profile of a third fluid in the porous sample by applying a mechanical load, and measuring, in each of the plurality of regions, a local saturation in the third fluid and a corresponding local electrical resistivity and/or conductivity after applying the mechanical load, the third fluid being advantageously identical with the first fluid;

the first fluid is a water-based fluid, in particular brine, the second fluid being an oil-based fluid;

the first fluid is a liquid, the second fluid being a gas;

the porous sample is a formation sample, in particular a rock sample.

The invention further concerns a system for determining a representative parameter of a porous sample, comprising:
a cell for receiving a porous sample containing a first fluid;
an apparatus for establishing a steady state profile of a second fluid content in the porous sample by applying a mechanical load, to create a plurality of regions having different second fluid contents in the porous sample;
a first measuring apparatus for measuring, in each of the plurality of regions, a local saturation in the first fluid or/and in the second fluid;
a second measuring apparatus for measuring, in each of the plurality of regions, a corresponding local electrical resistivity and/or conductivity;
a calculator for determining a value of the representative parameter based on the corresponding values of local saturation and of local electrical conductivity and/or resistivity in each of the plurality of regions.

The system according to the invention may comprise one or more of the following feature(s), taken solely or according to any technical feasible combination:
the first measuring apparatus is a nuclear magnetic resonance and/or a X-ray diffraction apparatus, the second measuring apparatus comprising several electrodes able to be placed on the porous sample.

BRIEF DESCRIPTION OF THE DRAWINGS

The invention will be better understood, upon reading of the following description, given only as an example, and made in reference to the following figures, in which.

DETAILED DESCRIPTION

Figure 1:
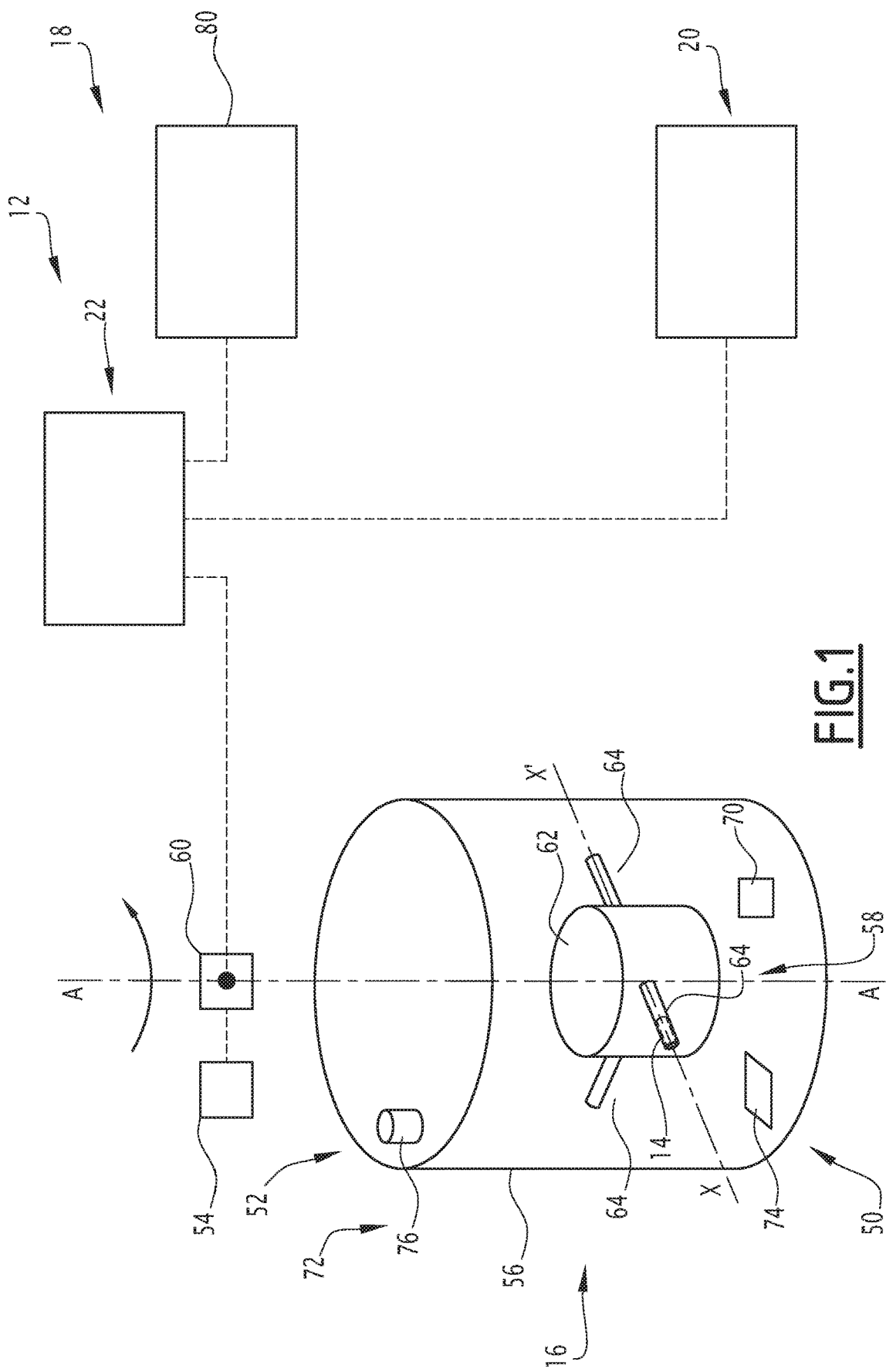
FIG. 1 is a schematic view of a system for carrying out a method according to the invention.
Figure 2:
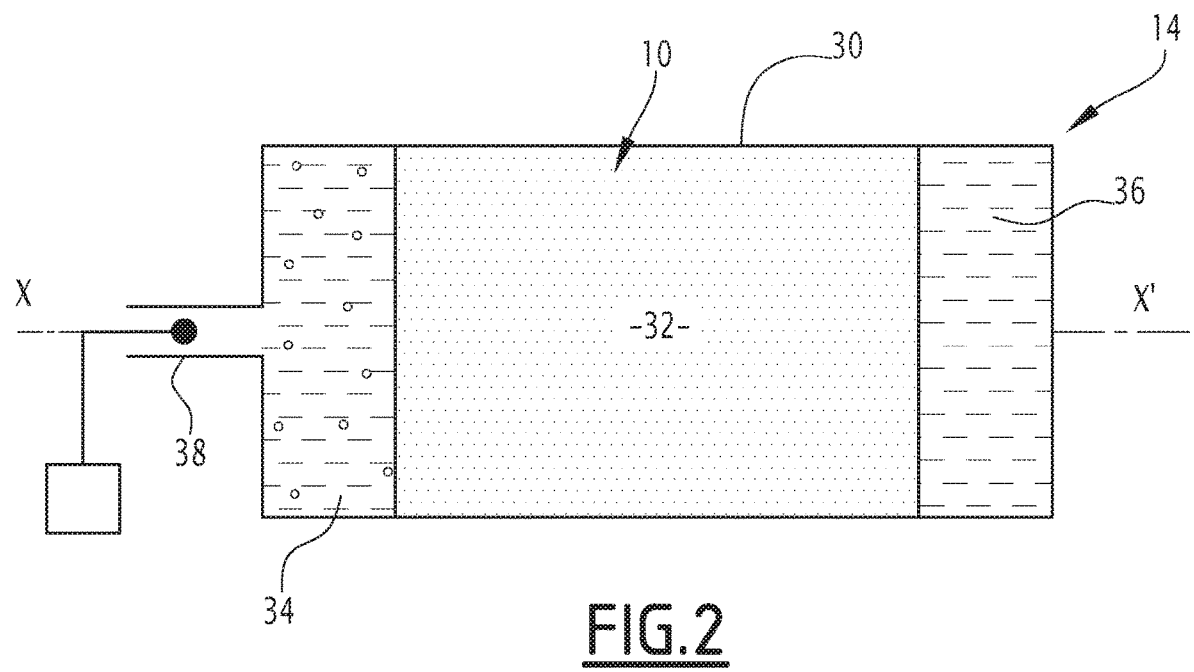
FIG. 2 is a schematic view of a cell containing a porous sample.

A method for determining a representative parameter of a porous sample 10 shown in FIG. 2 is carried out in a measuring system 12 schematically illustrated in FIGS. 1 and 2.

The porous sample 10 is for example a formation sample extracted from a sub-soil. The formation sample is in particular a rock sample having an internal porosity.

Typically, the porous sample 10 has for example a volume comprised between 8 cm$^3$ and 60 cm$^3$. It is advantageously cylindrical, with a circular cross-section.

The diameter of the porous sample 10 is generally comprised between 23 mm and 40 mm. Its length is for example comprised between 20 mm and 50 mm.

In a variant, the porous sample 10 is a parallelepiped.

The representative parameter is advantageously the exponent saturation coefficient n in Archie's law, and/or a capillary pressure Pc as a function of saturation $S_w$.

The measuring system 12 comprises a cell 14 receiving a porous sample 10 filled with a first fluid (see FIG. 2), and an apparatus 16 for establishing a steady state profile of a second fluid content in the porous sample 10 by applying a first mechanical load, to create a plurality of regions 17 having different second fluid contents in the porous sample 10.

The measuring system 12 further comprises a first measuring apparatus 18, for measuring, in each of the plurality of regions 17 (see FIG. 3), a local saturation $S_w$ in the first fluid or/and in the second fluid and a second measuring apparatus 20, for measuring, in each of the plurality of regions 17, a corresponding local electrical resistivity $R_t$ and/or conductivity $C_t$.

The measuring system 12 further comprises a calculator 22 for calculating the representative parameter based on the corresponding values of local saturation $S_w$ and local electrical conductivity $C_t$ and/or resistivity $R_t$ in each region of the porous sample 10.

An example of cell 14 is shown schematically in FIG. 2. It comprises a closed enclosure 30 defining a volume 32 for receiving the porous sample 10, an upstream chamber 34, for injection of the second fluid in the porous sample 10, and a downstream chamber 36 for receiving fluids collected when a mechanical load is applied to the porous sample 10.

The cell 14 delimits at least an inlet 38 for feeding the second fluid into the upstream chamber 34. It extends along a longitudinal axis X-X' which is coaxial with the longitudinal axis of the porous sample 10.

The inlet 38 is able to be closed to seal the enclosure 30. Chambers 34 and 36 are able to fluidly communicate to equilibrate pressures when fluid is produced from the porous sample 10 in either of the chambers 34, 36 as will be described below.

The cell 14 defines at least a transparent window in the downstream chamber 36 and/or in the upstream chamber 34.

Advantageously, the enclosure 30 of the cell 14 comprises an assembly of a centrifuge cup containing the porous sample 10 and of a transparent test tube delimiting the downstream chamber 36.

As shown in FIG. 1, the apparatus 16 here includes a centrifuge 50 to provide a mechanical load to the porous sample 10, a sensing system 52, and a control unit 54.

The centrifuge 50 comprises an enclosure 56, a rotor 58 rotatably mounted in the enclosure 50 around a rotation axis A-A', and a motor 60 able to drive the rotor 58 in rotation around axis A-A'.

The rotor 58 is contained in the enclosure 56. It is able to receive at least two cells 14, preferably at least three cells 14 containing porous samples 10.

In the example of FIG. 1, the rotor 58 comprises a central hub 62 and several radially protruding arms 64.

Each arm 64 receives a cell 14. The arms 64 are angularly distributed around the axis A-A'. The cell 14 is received with its longitudinal axis X-X' extending radially in reference to the rotation axis A-A'. The upstream chamber 34 is located relatively closer to the rotation axis A-A'. The downstream chamber 36 is located relatively away from the axis of rotation A-A'.

The motor 60 of the centrifuge 50 is able to be actuated by the control unit 54 to rotate the rotor 58 and jointly the cell 14 containing the porous sample 10 at a speed of rotation ranging from 500 rpm to 14000 rpm.

The mechanical load is therefore a centrifugal force applied on the porous sample 10.

The sensing unit 52 comprises a rotation speed sensor 70, able to detect the speed of rotation of the rotor 58, and a steady state detector 72.

The steady state detector 72 is able to monitor the rate of fluid production from the porous sample 10 during rotation of the cell 14 around the rotation axis A-A'.

In the example of FIG. 1, the steady state detector 72 comprises at least a stroboscope 74, and a camera 76 able to take images of the content of the downstream chamber 36 and/or of the upstream chamber 34 along time.

The control unit 54 is able to analyze the fluid production from the images taken with the camera 76 and to relate it to a rate of production of fluid in the downstream chamber 36 and/or in the upstream chamber 34 by image analysis.

The first measuring apparatus 18 is here a nuclear magnetic resonance apparatus. It is able to receive the porous sample 10 and to apply a variable magnetic field in the porous sample 10 to scan successive regions 17 of the porous sample 10 having different contents in second fluid.

Figure 3:
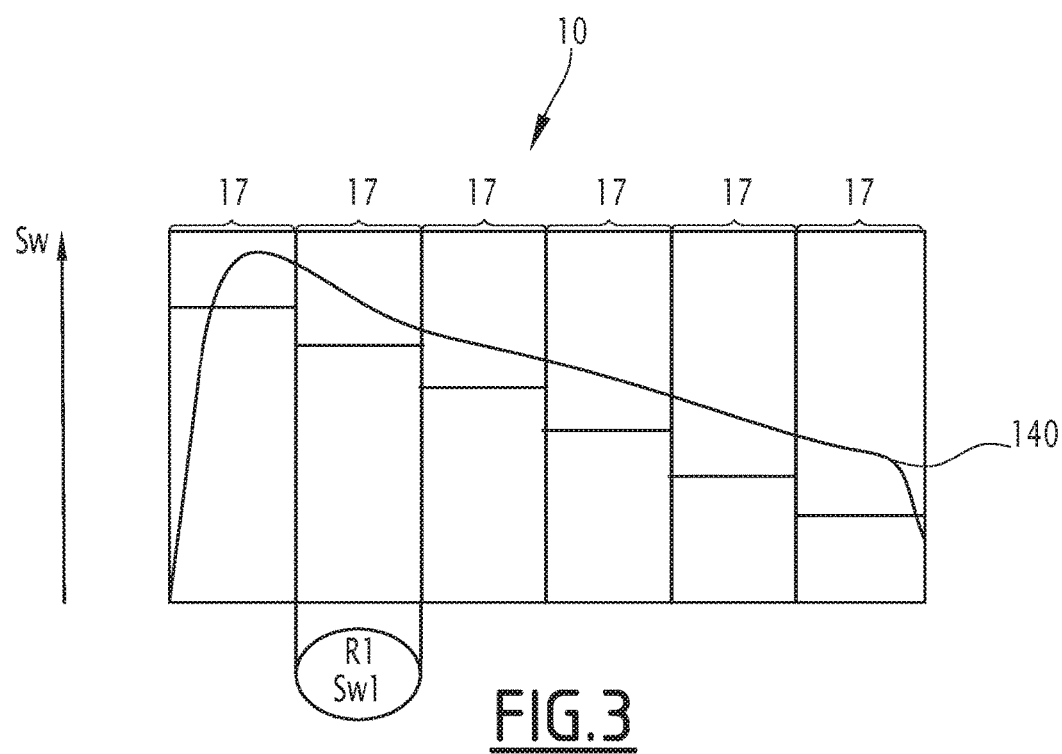
FIG. 3 is a schematic view of the porous sample, illustrating a first steady state profile of fluid saturation in the sample.

In the example of FIG. 3, the successive regions 17 are slices of the porous sample 10 taken in succession longitudinally along the length of the porous sample 10. Each slice is delimited by two parallel transverse planes which are perpendicular to the longitudinal axis X-X' of the porous sample 10. The number of regions 17 is for example comprised between 4 and 10 preferably between 5 and 8. The length of each region 17, taken along the axis is preferably smaller than 20% of the total length of the porous sample 10.

Based on the nuclear magnetic resonance signal measured in each region 17, the apparatus 18 is able to determine the local saturation in first fluid and/or second fluid in each region 17, in the steady state profile of fluid content in the porous sample 10.

The second measuring apparatus 20 comprises a plurality of electrodes applied on the porous sample 10 around the successive regions 17.

A voltage can be applied to the electrodes to determine a resistivity and/or a conductivity of each region 17 along the length of the porous sample 10, each region 17 corresponding to a region 17 in which the saturation in first fluid and/or second fluid was determined by the first measuring apparatus 18.

The calculator 22 is able to collect the values of saturations determined by the first measuring apparatus 18 and the values of conductivities and/or resistivities measured by the second measuring apparatus 20, for each region 17, and to determine the representative parameter.

For example, the calculator 22 is able to calculate the logarithm of the ratio RI of the resistivity $R_t$ measured in each region 17 by the second measuring apparatus 20 to the resistivity $R_o$ of the porous sample 10 filled only with the first fluid, and to correlate it to the logarithm of the saturation $S_w$ in first fluid in each region 17, as determined by the apparatus 20. Based on this correlation, the calculator 22 is able to determine a slope of the curve of $\log(R_t/R_o)$ as a function of $\log(S_w)$, for example by linear regression, to calculate the saturation exponent of Archie's Law.

Similarly, based on the position of each region 17 along the porous sample axis, and on the rotation speed, the calculator 22 is able to calculate the capillary pressure Pc applied in each region using the following equation:

$$Pc = \tfrac{1}{2} \times \omega^2 \times \Delta\rho \times (r_s^2 - r_o^2)$$

in which $\omega$ is the rotation speed, $\Delta\rho$ is the difference of density between the first fluid and the second fluid, $r_s$ is the radius separating the region 17 from the axis of rotation A-A', and $r_0$ is the radius separating the axis of rotation A-A' from the surface of the porous sample 10 farthest (in drainage) or closest (in imbibition) to the axis of rotation A-A'.

The calculator 22 is then able to determine a plot of the capillary pressure Pc as a function of the saturation in the first fluid $S_w$.

A method for determining a representative parameter of a porous sample 10, using the system 12 will be now described.

Initially, the porous sample 10 is saturated with a first fluid, in particular with a water-based fluid such as brine.

The resistivity $R_o$ of the porous sample 10 saturated with the first fluid is measured, for example using the second measuring apparatus 20 or using an external apparatus.

Then, the porous sample 10 filled with the first fluid is inserted into the porous sample reception volume 32 of the cell 14.

The cell 14 is introduced in the centrifuge 50. It is placed in an arm 64 of the rotor 58 with the axis X-X' of the porous sample 10 extending radially with regards to the axis of rotation A-A' of the rotor 58.

A second fluid is introduced in the upstream chamber 34 located closer to axis A-A'. The second fluid is for example oil, or gas (for example air).

Then, the control unit 54 of the centrifuge 50 is activated to actuate the motor 60 and rotate the rotor 58 jointly with the porous sample 10 contained in the cell 14 around the rotation axis A-A'. A first mechanical load applies on the porous sample 10 due to the centrifugal force applying on the porous sample 10.

The axis X-X' of the porous sample 10 extending radially with regard to the rotation axis A-A', the second fluid contained in the upstream chamber 54 progressively penetrates into the porous sample 10 to generate a profile of saturation in the second fluid which is represented schematically with curve 140 in FIG. 3. In FIG. 3, the rotation axis of the porous sample 10 is located on the right of the porous sample 10.

The steady state detector 72 of the sensing unit 52 is activated to measure the rate of fluid extraction from the porous sample 10 collected in the downstream chamber 36.

In a time period comprised generally between 1 hours and 10 days, a second fluid content steady state profile establishes in the porous sample 10, when the rate of fluid extraction measured by the steady state detector 72 becomes zero.

In the steady state profile, the porous sample 10 comprises successive regions 17 along the longitudinal axis X-X', the successive regions 17 having different local average values of saturation $S_w$, in particular increasing values of saturation in the first fluid $S_w$ along the length of the porous sample 10, taken from the end of the porous sample 10 located closer to the axis A-A' (on the right in FIG. 3) to the end of the porous sample 10 located further away from the axis A-A' (on the left in FIG. 3).

The porous sample 10 is then transferred to the first measuring apparatus 18.

The apparatus 18 determines an average saturation in first fluid $S_w$ and/or in second fluid in each of several successive regions 17 of the porous sample 10, taken along the porous sample 10 longitudinal axis X-X'. Each saturation $S_w$ is collected and sent to the calculator 22.

Then, the porous sample 10 is equipped with the second measuring apparatus 20 to carry out a measurement of a plurality of conductivities and/or resistivities $R_t$ in the same regions 17 where the saturations $S_w$ were determined by the first measuring apparatus 18.

The electrodes 17 are activated to measure for example the resistivity $R_t$ of each region 17.

The values of resistivities $R_t$ are collected and sent to the calculator 22.

Figure 4:
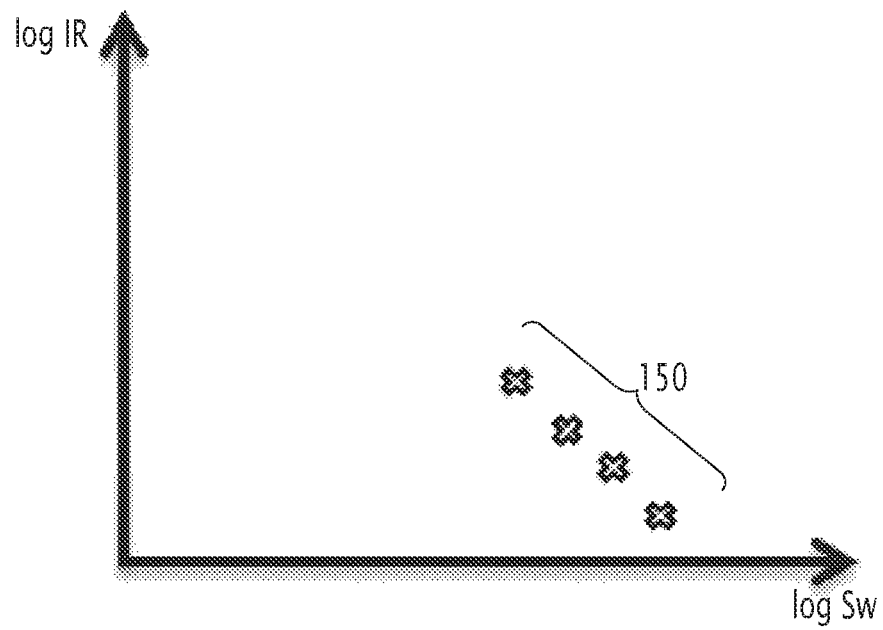
FIG. 4 is a logarithmic plot of the resistivity index versus saturation, obtained by carrying out a first phase of the method according to the invention.

Then, the calculator 22 calculates, for each region 17, the logarithm of the ratio RI of the resistivity $R_t$, as measured by the apparatus 20, to the resistivity at saturation in first fluid $R_o$. It calculates the logarithm of saturation $S=_w$ in first fluid in each region 17. It then correlates and plots the pairs 150 of calculated logarithm of RI and logarithm of $S_w$, to determine a slope of the curve of log (RI) as a function of log ($S_w$) as shown in FIG. 4, for example by least square analysis. The exponent coefficient of Archie's law n is then deduced from the slope of the curve.

Figure 5:
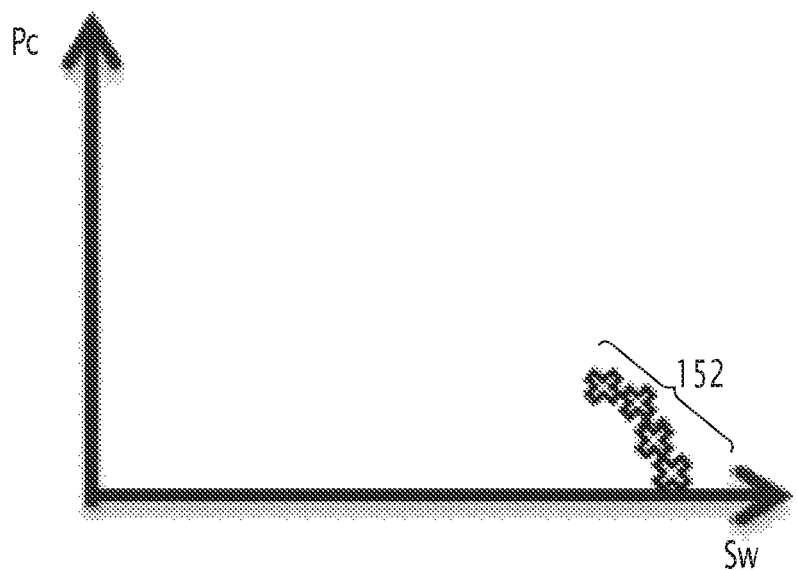
FIG. 5 is a plot of the capillary pressure versus saturation, obtained by carrying out a first phase of the method according to the invention.

Similarly, the calculator 22 calculates the profile 152 of capillary pressure Pc as a function of saturation $S_w$ based on the measurements made in the same porous sample 10 at various regions 17 of the porous sample 10 when a steady state fluid content profile is obtained in the porous sample 10, as shown in FIG. 5.

If the number of points in each curve of FIG. 4 and FIG. 5 is not enough to obtain sufficient accuracy, the porous sample 10 can be then placed again in the apparatus 16 for establishing a modified fluid content steady state profile.

The speed of rotation of the porous sample 10 is for example increased to create a mechanical load having an intensity different from the intensity of the first mechanical load.

Figure 6:
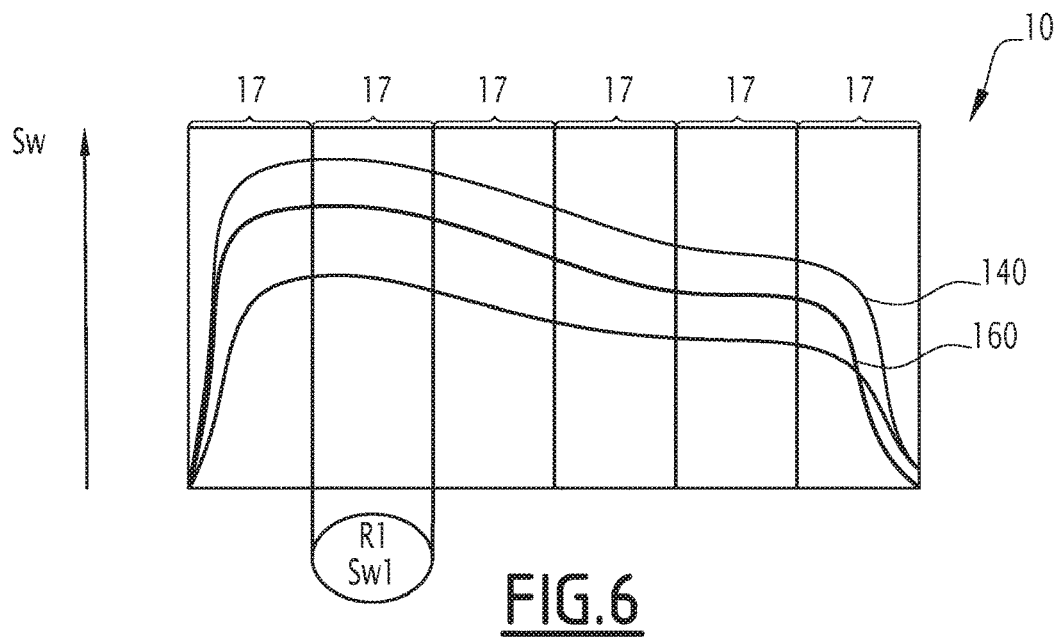
FIG. 6 is a schematic view of the porous sample, illustrating a second steady state profile of fluid saturation in the sample.
Figure 7:
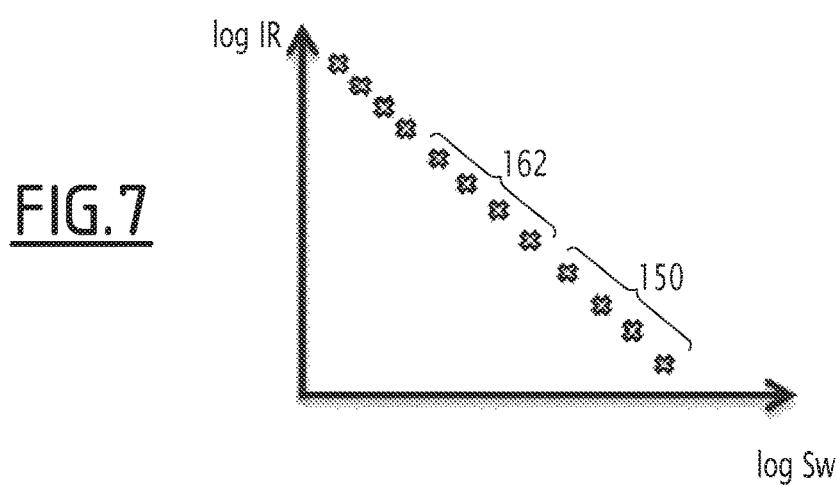
FIG. 7 is a logarithmic plot of the resistivity index versus saturation, obtained by carrying out a second phase of the method according to the invention.
Figure 8:
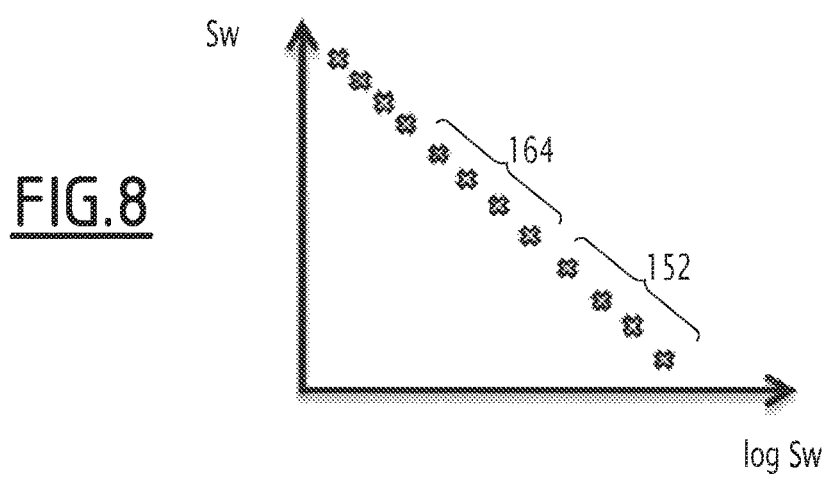
FIG. 8 is a plot of the capillary pressure versus saturation, obtained by carrying out a second phase of the method according to the invention.

After a steady state is reached, a second fluid content steady state profile is established (see curve 160 in FIG. 6) and the saturation $S_w$ in first fluid in each region 17 is again measured by the apparatus 20 as described before. Similarly, the resistivity $R_t$ in each region 17 is determined and more points (see points 162 and 164 respectively in FIGS. 7 and 8) can be obtained on each of the curves, as shown in FIGS. 7 and 8.

The same operations can be repeated several times.

The method according to the invention therefore allows a significant number of values of saturations $S_w$ at steady state in a porous sample 10 to be obtained simultaneously with a corresponding number of measurements of the resistivity $R_t$ and/or conductivity of the porous sample 10.

This leads to obtaining many points on a curve relating the logarithm of the ratio RI of the resistivity $R_t$ to the resistivity at saturation $R_o$ to the logarithm of saturation $S_w$, and hence a determination of the exponent coefficient n of Archie's law.

The determination is fast, for example in the order of a few days. This drastically reduces the time necessary to determine relevant parameters of the porous sample 10. The results of the measurements can be provided to the operations in a few weeks, as opposed to several months in using state of the art techniques.

The results can then be integrated in the field study, after the drilling of a well has been made. The calculation of potential reservoir capabilities is made at an early stage, which is extremely favorable in terms of further operations in the field.

The method according to the invention is easy to carry out, and does not require a large amount of man force, and/or numerous porous samples 10.

The method being based on a steady state analysis of the porous sample 10, it does not comprise biases which could arise from methods in which the porous sample 10 is in a transitory state in its fluid content.

Moreover, the method according to the invention is able to determine simultaneously the exponent coefficient n of Archie's law, and the profile of a capillary pressure Pc variation as a function of the fluid saturation $S_w$.

Figure 10:
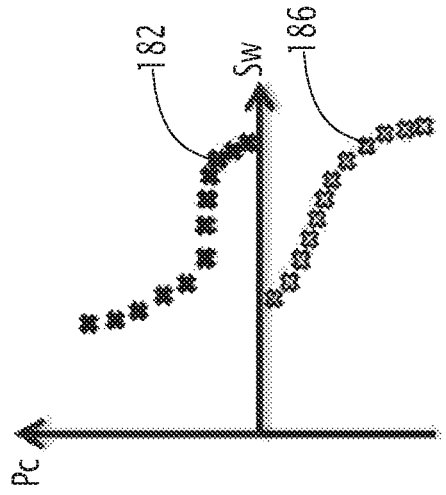
FIG. 10 is a plot of the capillary pressure versus saturation, obtained by carrying out a cycle of imbibition and drainage with the method according to the invention.
Figure 11:
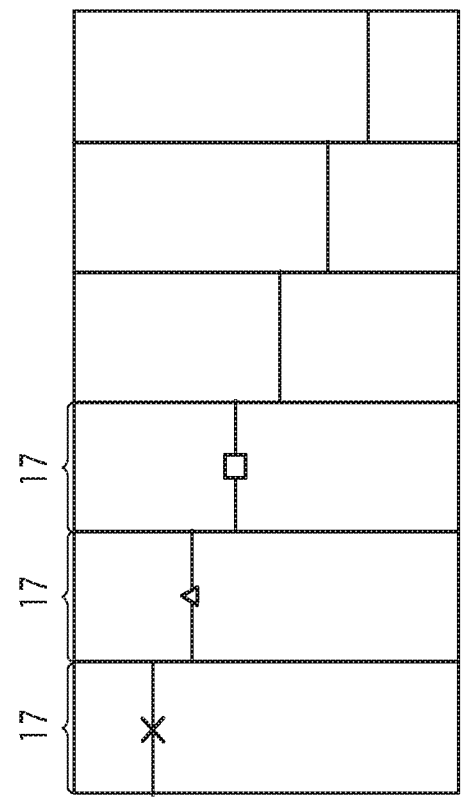
FIGS. 11 and 12 are view similar to FIGS. 3 and 4, illustrating a variant of the method according to the invention.
Figure 9:
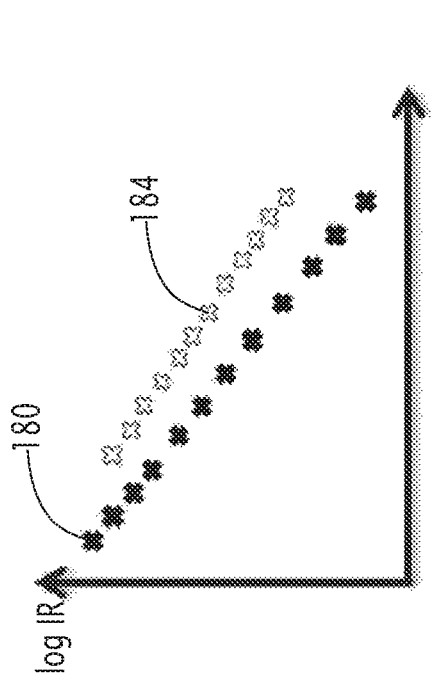
FIG. 9 is a logarithmic plot of the resistivity index versus saturation, obtained by carrying out a cycle of imbibition and drainage with the method according to the invention.

In a variant, shown in FIGS. 9 and 10, a draining of the second fluid is carried out after the imbibition of the porous sample 10 has been carried out with the second fluid.

The draining of the second fluid is for example carried out with a third fluid, which is advantageously identical to the first fluid.

For example, after the imbibition of a porous sample 10 saturated with brine as a first fluid, with oil as a second fluid, brine can be used again as a third fluid to drain out oil from the porous sample 10.

The sensing unit 52 of the apparatus 16 is then configured to monitor the rate of second fluid extraction into the upstream chamber 34.

The porous sample 10 is inserted in the apparatus 16 and is rotated so that the second fluid drains out of the porous sample 10.

A fluid content steady state profile is established in the porous sample 10 and is monitored by the sensing unit 52. Once the steady state has been obtained, the porous sample 10 is introduced successively in the first measuring apparatus 18 and in the second measuring apparatus 20 as described previously to obtain further points of the previously described curves.

As shown in FIGS. 9 and 10, a hysteresis in the curves of the logarithm of the ratio RI versus the logarithm of the saturation $S_w$ obtained respectively in the imbibition phase (curve 180) or and in the draining phase (curve 184) is observed, as shown in FIG. 9.

Similarly, a hysteresis is also observed in the curves 182, 186 of capillary pressure Pc as a function of the saturation $S_w$, as shown in FIG. 10.

Figure 12:
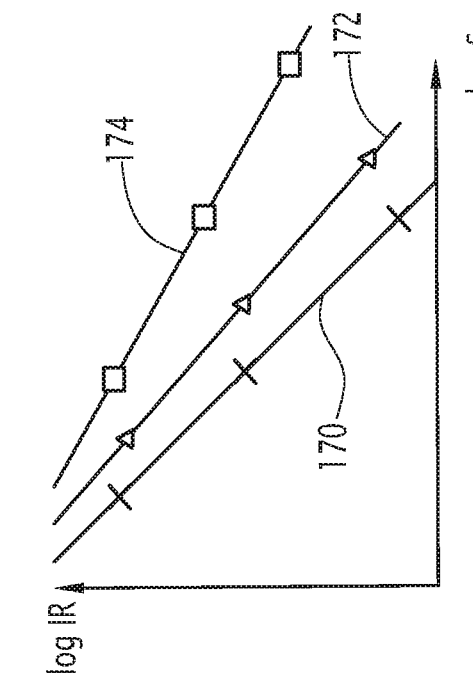

In another variant, shown in FIG. 12, several plots of log RI versus log $S_w$, each corresponding to one specific region 17A, 17B, 17C undergoing different steady states at different mechanical loads applied to the porous sample 10 are plotted separately as shown in FIG. 12.

This leads to determining a specific value of the exponent coefficient n of Archie's law in each specific region 17A, 17B, 17C of the porous sample 10. For example, the n exponent coefficient for a first region 17A is determined by the plot 170 drawn with crosses in FIG. 12, the n exponent coefficient for a second region 17B is determined by the plot 172 drawn with triangles in FIG. 12, and the n exponent coefficient for a third region 17C is determined by the plot 174 drawn with squares in FIG. 12.

Figure 13:
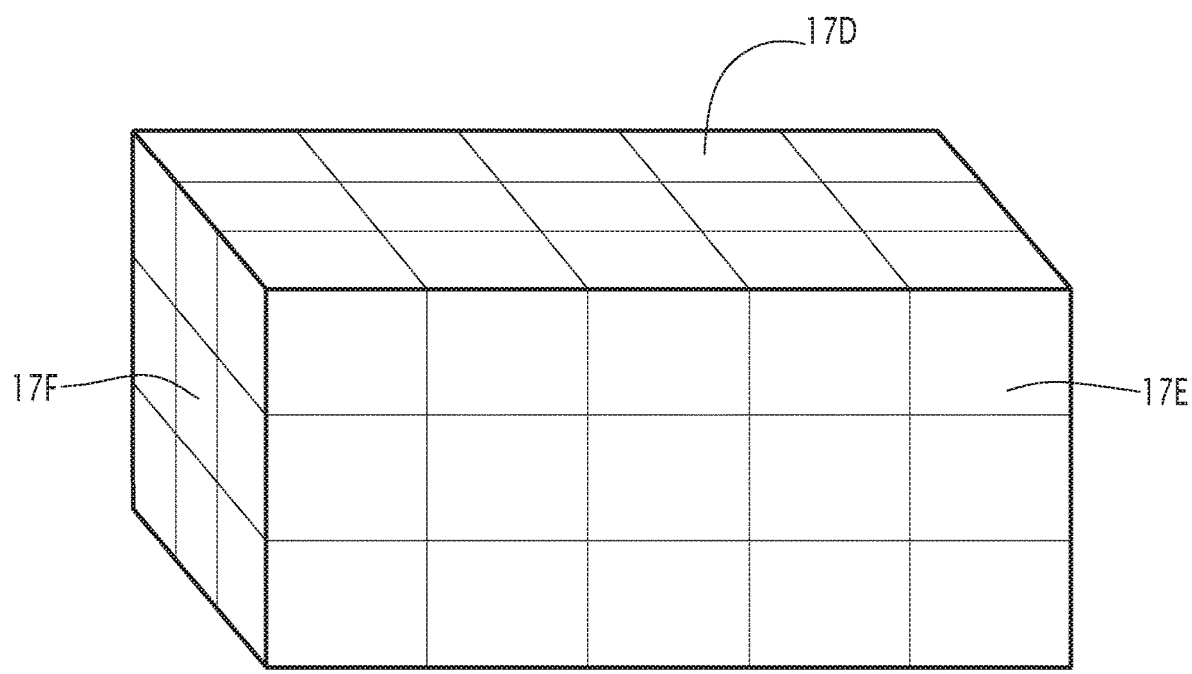
FIG. 13 is a view similar to FIG. 3, for another variant of method according to the invention.

In another variant, the regions 17A, 17B, 17C are not slices, but are pixels delimited in the sample as shown in FIG. 13, schematically with regions 17D, 17E, 17F.

For such a case, the first measuring apparatus 18 is able to measure local saturations in each of the regions 17D, 17E, 17F. The second measuring apparatus 20 is for example an electrical resistivity tomography apparatus.

In another variant, the first fluid and/or the second fluid is a gas, the second fluid and/or the first fluid being a liquid.

In another variant, the first measuring apparatus 18 is an X-ray spectrograph.

The invention claimed is:

1. A method of determining a representative parameter of a porous sample, comprising:
   providing a porous sample comprising a longitudinal axis, the porous sample containing a first fluid;
   applying a first mechanical load to establish a steady state profile of a second fluid content in the porous sample, and to create a plurality of regions having different second fluid contents in the porous sample, the successive regions being slices of the porous sample taken in succession longitudinally along a length of the porous sample, each slice being delimited by two parallel transverse planes which are perpendicular to the longitudinal axis of the porous sample;
   measuring, in each of the plurality of regions, a local saturation in the first fluid or/and in the second fluid;
   measuring, in each of the plurality of regions, a corresponding local electrical resistivity and/or a corresponding local electrical conductivity; and
   determining a value of the representative parameter based on the corresponding values of the local saturation and of the local electrical conductivity and/or the local electrical resistivity in each of the plurality of regions.

2. The method according to claim 1, wherein the representative parameter is an exponent coefficient a saturation in Archie's law.

3. The method according to claim 2, wherein determining the representative parameter comprises calculating a slope of a curve of a logarithm resistive index calculated from the local resistivity measured in a plurality of regions, as a function of a logarithm of the local saturation in the first fluid or/and in the second fluid in each of the plurality of regions.

4. The method according to claim 1, wherein applying the first mechanical load comprises centrifuging the porous sample.

5. The method according to claim 1, wherein measuring, in each of the plurality of regions, of a local saturation in the first fluid or/and in the second fluid comprises carrying out nuclear magnetic resonance or/and by X-ray diffraction.

6. The method according to claim 1, wherein the measuring, in each of the plurality of regions, the corresponding local electrical resistivity and/or the corresponding local electrical conductivity comprises placing electrodes locally at the boundaries of the region.

7. The method according to claim 1, wherein establishing a steady state profile in the porous sample comprises saturating the porous sample with the first fluid, and progressively introducing the second fluid in the porous sample while applying the first mechanical load.

8. The method according to claim 1, wherein establishing the steady state profile comprises measuring a rate of second fluid and/or first fluid extracted from the porous sample.

9. The method according to claim 1, comprising measuring a plurality of local saturations in the first fluid or/and in the second fluid and measuring a plurality of local electrical conductivities and/or local electrical resistivities, and after measuring the plurality of local saturations in the first fluid or/and in the second fluid and after measuring the plurality of local electrical conductivities and/or local electrical resistivities, applying an additional mechanical load to the porous sample to obtain a modified steady state profile of content in the second fluid, the additional mechanical load having an intensity different from the first mechanical load, and measuring, in each of the plurality of regions, an additional local saturation in the first fluid or/and in the second fluid and a corresponding local electrical resistivity and/or a corresponding local electrical conductivity after applying the additional mechanical load.

10. The method according to claim 1, comprising measuring a plurality of local saturations in the first fluid or/and in the second fluid and measuring a plurality of local electrical conductivities and/or local electrical resistivities, and after measuring the plurality of local saturations in the first fluid or/and in the second fluid and after measuring the plurality of local electrical conductivities and/or local electrical resistivities, establishing a fluid content steady state profile of a third fluid in the porous sample by applying a further mechanical load, and measuring, in each of the plurality of regions, a local saturation in the third fluid and a corresponding local electrical resistivity and/or a corresponding local electrical conductivity after applying the further mechanical load.

11. The method according to claim 1, wherein the first fluid is a water-based fluid, the second fluid being an oil-based fluid.

12. The method according to claim 1, wherein the first fluid is a liquid, the second fluid being a gas.

13. The method according to claim 1, wherein the porous sample is a formation sample, in particular a rock sample.

14. A system of determination of a representative parameter of a porous sample, comprising:
- a cell configured to receive a porous sample containing a first fluid;
- an apparatus configured to establish a steady state profile of a second fluid content in the porous sample by applying a mechanical load, to create a plurality of regions having different second fluid contents in the porous sample;
- a first measuring apparatus configured to measure, in each of the plurality of regions, a local saturation in the first fluid or/and in the second fluid;
- a second measuring apparatus configured to measure, in each of the plurality of regions, a corresponding local electrical resistivity and/or a corresponding local electrical conductivity; and
- a calculator configured to determine a value of the representative parameter based on the corresponding values of local saturation and of the local electrical conductivity and/or the local electrical resistivity in each of the plurality of regions.

15. The system according to claim 14, wherein the first measuring apparatus is a nuclear magnetic resonance and/or a X-ray diffraction apparatus, the second measuring apparatus comprising several electrodes configured to be placed on the porous sample.

16. The method according to claim 10, wherein the third fluid is identical with the first fluid.

17. The method according to claim 11, wherein the first fluid is brine.

18. The system according to claim 14, wherein the porous sample is a rock sample.

19. A method of determining a representative parameter of a porous sample, comprising:
- providing a porous sample, the porous sample containing a first fluid;
- applying a first mechanical load to establish a steady state profile of a second fluid content in the porous sample, and to create a plurality of regions having different second fluid contents in the porous sample;
- measuring, in each of the plurality of regions, a local saturation in the first fluid or/and in the second fluid;
- measuring, in each of the plurality of regions, a corresponding local electrical resistivity and/or a corresponding local electrical conductivity, comprising placing electrodes locally at the boundaries of the region; and
- determining a value of the representative parameter based on the corresponding values of the local saturation and of the local electrical conductivity and/or the local electrical resistivity in each of the plurality of regions.

* * * * *